United States Patent [19]

Ishitsu et al.

[11] Patent Number: 5,042,976
[45] Date of Patent: Aug. 27, 1991

[54] BALLOON CATHETER AND MANUFACTURING METHOD OF THE SAME

[75] Inventors: Yoshio Ishitsu; Kouji Tsuchida; Shigekazu Sekii, all of Fuji, Japan

[73] Assignee: Terumo Kabushiki Kaisha, Tokyo, Japan

[21] Appl. No.: 391,503

[22] PCT Filed: Jan. 12, 1988

[86] PCT No.: PCT/JP88/00023
§ 371 Date: Jul. 10, 1989
§ 102(e) Date: Jul. 10, 1989

[87] PCT Pub. No.: WO88/05316
PCT Pub. Date: Jul. 28, 1988

[30] Foreign Application Priority Data

Jan. 13, 1987 [JP] Japan ................... 62-5823
Jan. 13, 1987 [JP] Japan ................... 62-5824
Jun. 25, 1987 [JP] Japan ................. 62-158143
Jun. 25, 1987 [JP] Japan ................. 62-158145

[51] Int. Cl.$^5$ ............................................. A61M 25/00
[52] U.S. Cl. ..................................... 604/96; 604/100; 606/192
[58] Field of Search ........................... 604/96–103, 604/282; 600/18; 606/192–196

[56] References Cited

U.S. PATENT DOCUMENTS

| 2,930,377 | 3/1960 | Cowley . | |
|---|---|---|---|
| 3,143,651 | 3/1979 | Patel | 604/100 |
| 3,448,739 | 6/1969 | Stark et al. | 604/103 |
| 3,746,003 | 7/1973 | Blake et al. | 604/100 |
| 3,833,003 | 9/1974 | Taricco | 606/192 |
| 3,833,004 | 10/1974 | Vazquez et al. | 604/100 |
| 3,985,601 | 10/1976 | Panagrossi . | |
| 4,157,094 | 6/1979 | Patel | 604/98 |
| 4,177,815 | 12/1979 | Patel | 604/103 |
| 4,465,072 | 8/1984 | Taheri . | |
| 4,651,751 | 3/1987 | Swendson et al. | 128/786 |
| 4,661,095 | 4/1987 | Taller et al. . | |
| 4,762,128 | 8/1988 | Rosenbluth | 604/96 |

FOREIGN PATENT DOCUMENTS 45-5239   2/1970   Japan .
51-22756  7/1976   Japan .
1154950   6/1969   United Kingdom .

Primary Examiner—John D. Yasko
Assistant Examiner—Anthony Gutowski
Attorney, Agent, or Firm—Frishauf, Holtz, Goodman & Woodward

[57] ABSTRACT

A balloon catheter is provided, which comprises a catheter body made of a flexible tube provided with at least one inner channel and with an annular groove formed on an outer surface near the distal end portion of the tube, and a balloon covering the annular groove in such a manner that the outer diameter of the balloon is equal to or smaller than a maximum diameter of the distal end portion of the tube, the balloon being expanded or shrunk through another inner channel. A method of manufacturing the balloon catheter which comprises the steps of reducnig an outer diameter of a distal end portion of the catheter body while keeping a desired inner channel undamaged, mounting a tubular heat-resistant member to a prospective balloon mounting portion of the reduced diameter portion, molding a reduced diameter portion extruded from the heat-resistant member into a spherical shape, and mounting an inflatable balloon to the balloon mounting portion after removing the heat-resistant member.

12 Claims, 4 Drawing Sheets

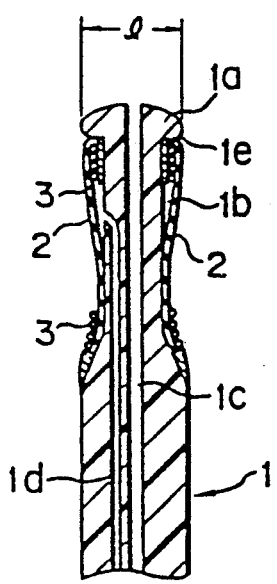
F I G. 1
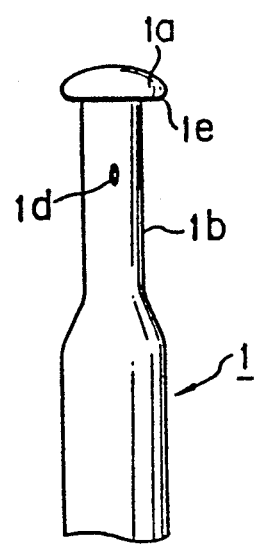
F I G. 2
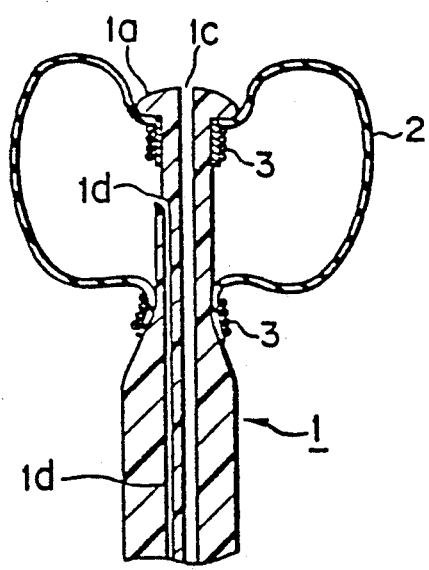
F I G. 3
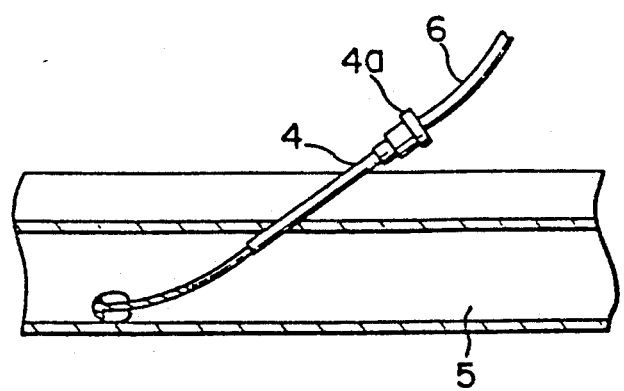
F I G. 4

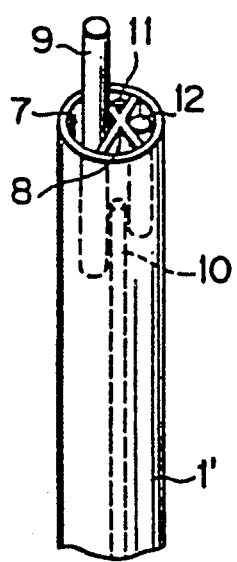
F I G. 5A
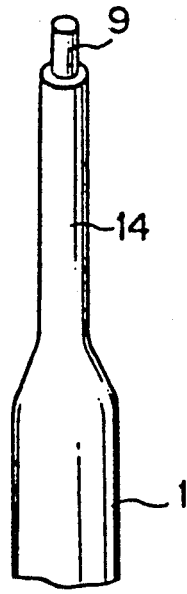
F I G. 5B
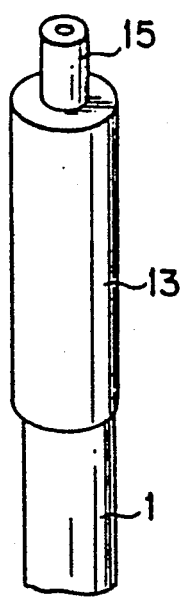
F I G. 5C

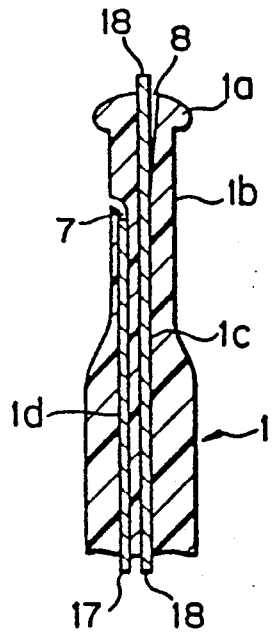
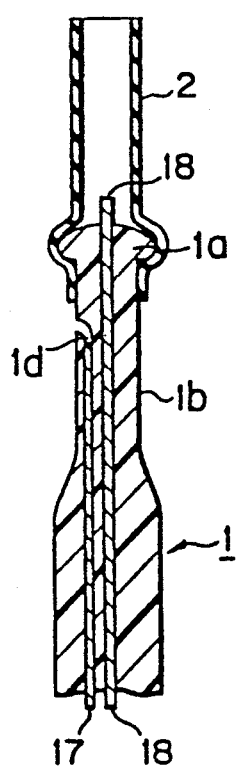
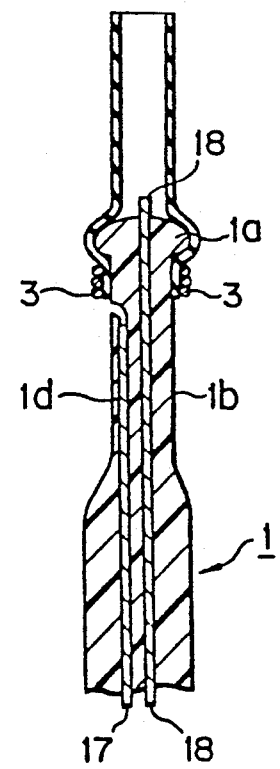
FIG. 6A     FIG. 6B     FIG. 6C
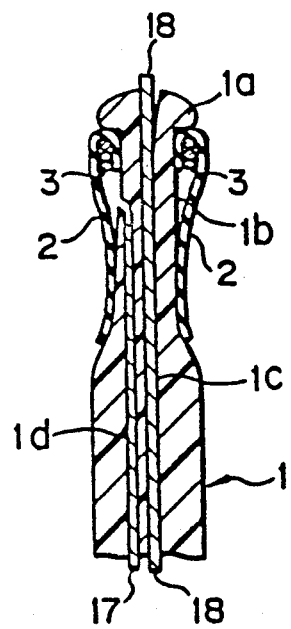
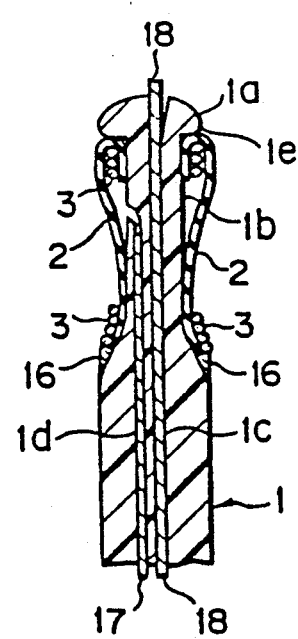
FIG. 6D     FIG. 6E

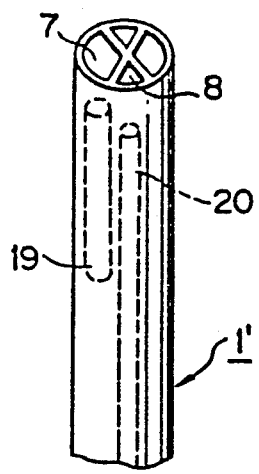 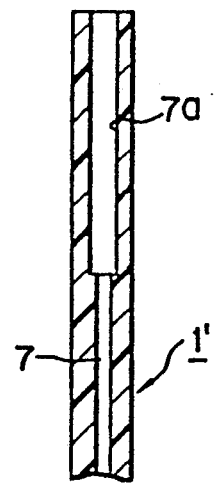 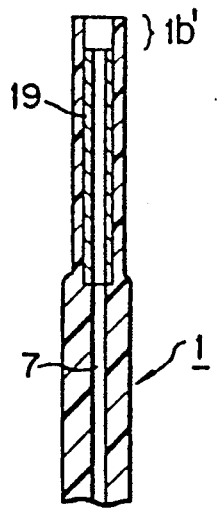
F I G. 7A  F I G. 7B  F I G. 7C
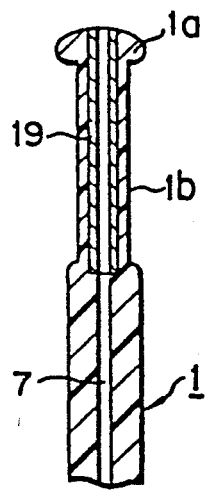 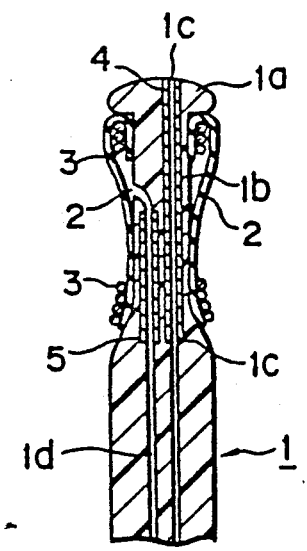
F I G. 7D  F I G. 8

BALLOON CATHETER AND MANUFACTURING METHOD OF THE SAME

TECHNICAL FIELD

The present invention relates to a balloon catheter for intravascular indwelling which has an inflatable balloon at its distal end, and a method of manufacturing the same.

PRIOR ART

The distal end portion of a conventional balloon catheter for intravascular indwelling of this type is inserted in a blood vessel by using an insertion tool such as an introducer, and the balloon catheter is indwelled in a predetermined portion. In this state, measurements, therapy, and the like are generally performed.

The outer diameter (before inflation) of the balloon attached to a conventional balloon catheter is larger than that of the catheter, and the balloon is exposed outside. When the balloon catheter is to be inserted into a blood vessel, the balloon is caught by a check valve or the inner wall of the insertion equipment and is undesirably damaged.

In another conventional balloon catheter, the outer diameter of the distal end portion of a catheter is set to be smaller than that of the remaining portion of the catheter and a balloon is mounted on the small-diameter portion. Although the catheter can be inserted into a blood vessel by using a sheath having the same diameter as that of the catheter and a blood vessel is not so damaged, the outer diameter of the balloon is larger than that of the distal end portion of the catheter at the upper end portion of the balloon and a step is formed between the balloon and the distal end of the catheter. The balloon tends to be brought into direct contact with a check valve or the like arranged at an insertion port of blood vessel insertion equipment and may be damaged. In still another conventional balloon catheter, the boundary portions of the upper end of a balloon and the distal end of a catheter are potted by an adhesive and the distal end portion of the catheter is smoothly coupled to the balloon mounting surface.

In this case, damage to the balloon can be eliminated. However, since the outer diameter of the balloon is larger than that of the distal end of the catheter, a sheath having a diameter corresponding to the balloon diameter larger than that of the catheter must be used and a blood vessel tends to be damaged by the catheter. In addition, since the potted portions are not formed of the same material as that of the potted members, peeling of the adhered portions occurs. Thus, a danger caused by intravascular indwelling of the catheter cannot be perfectly eliminated.

The diameter of the balloon catheter for intravascular indwelling of this type is very small, and therefore it is difficult to mass-produce the structure in which the diameter of the balloon is set to be smaller than that of the adjacent catheter.

It is an object of the present invention to provide a compact balloon catheter and a method of manufacturing the same, wherein a balloon mounted on the catheter will not be caught and damaged by a check valve or inner wall member of blood vessel insertion equipment, and a sheath having a diameter larger than the catheter need not be used during insertion, thereby preventing damage to the blood vessel.

It is another object of the present invention to provide a balloon catheter which does not damage an inner wall of a blood vessel and in which a balloon can be symmetrically inflated.

It is still another object of the present invention to provide a balloon catheter and a method of manufacturing the same, which are free from natural contraction of the inner cavity at the distal end portion of the catheter as well as contraction or deformation of the inner cavity (e.g., a balloon cavity or a pressure cavity) which is caused by a tensile force of a string for mounting the balloon.

DISCLOSURE OF THE INVENTION

According to an aspect of the present invention, there is provided a balloon catheter comprising: a catheter body formed as a single member and made of a flexible tube provided with at least one inner channel with an opening at a distal end portion thereof, the catheter body being provided with an annular groove formed on an outer surface of the tube adjacent to the distal end portion along a circumferential direction of the tube and having a predetermined length along an axial direction of the tube and with a balloon inflation inner channel open to a bottom portion of the annular groove; and a balloon for covering the bottom portion of the annular groove, the balloon being arranged in the annular groove such that a diameter is equal to or smaller than a maximum outer diameter of the distal end portion of the tube.

According to another aspect of the present invention, there is provided a method of manufacturing a balloon catheter, comprising the steps of: forming a prospective balloon mounting portion and a prospective catheter distal end forming portion extending toward the extreme end from the prospective balloon mounting portion by reducing an outer diameter of a distal end portion of a balloon catheter body made of a thermo-plastic material and having a predetermined inner channel, thereby forming a small-diameter portion while allowing the predetermined inner channel to remain therein; inserting a tubular heat-resistant member into the prospective balloon mounting portion of the small-diameter portion and protecting the prospective balloon mounting portion, the tubular heat-resistant member having an inner diameter substantially the same as an outer diameter of the small-diameter portion; forming the prospective catheter distal end forming portion extending from the tubular heat-resistant member into a catheter distal end shape; and mounting an inflatable balloon to the prospective balloon mounting portion after the tubular heat-resistant member is removed.

An upper edge of the wall surface defining the annular groove and contacting the distal end portion of the tube is preferably a smooth curved surface. The distal end portion of the tube is preferably smoothly arcuated or flat. These portions can be formed by heat molding or ultrasonic machining.

Reduction of the diameter of the distal end portion is performed by inserting a heat-resistant rod or tubular member into an inner channel adapted to be left as a cavity for measurements (e.g., a blood pressure) or a balloon inflation cavity and by heating the resultant structure.

The tubular heat-resistant member to be inserted into the prospective balloon mounting portion is preferably dividable along the longitudinal direction.

A tubular reinforcing member made of a heat-resistant plastic, a ceramic or a metal may be embedded beforehand in the inner channel (an inner cavity) of an area including at least an annular groove formation range serving as the balloon mounting portion so as to cause the reinforcing member to communicate with other portions in the inner cavity. In this case, the inner diameter of the tubular reinforcing member is substantially the same as that of the inner cavity which communicates with it. A connecting portion between the reinforcing member and the inner cavity is preferably flat.

The tubular reinforcing member is preferably inserted in a predetermined inner cavity of a balloon catheter body having a plurality of inner cavities prior to the reduction of the diameter of the distal end portion of the catheter. Subsequently, the distal end including a position corresponding to the balloon mounting portion is preferably subjected to distal end working including reduction of its diameter. Finally, the balloon is mounted on the balloon mounting portion while the reinforcing member is left in the predetermined inner cavity.

The step of mounting the balloon may include the steps of: inserting a rod or pipe member having substantially the same outer diameter as the inner diameter of the inner channel into the inner channel to assure the inner diameter of the inner channel; placing one end of a balloon tube at one end of the annular groove of the distal end portion of the catheter body; fixing one end of the balloon tube to one end of the annular groove by an adhesive or a string which is wound around one end of the balloon tube; turning the balloon tube inside out and fitting the balloon tube in the annular tube; and fixing the other end of the balloon tube to the other end of the annular groove by an adhesive or a string which is wound around the other end of the balloon groove. Both the end portions of the balloon tube constitute a substantially continuous flat surface together with the distal end portion of the catheter body and the balloon tube rear adhesion portion of the catheter body.

The substantially continuous, flat surfaces of the connecting portions between the two ends of the balloon tube and the catheter body may be formed in the following manner. A potting material is filled in the boundary portion between the balloon tube and the distal end of the catheter body or between the balloon tube and the rear adhesion portion of the catheter body. Alternatively, a string may be wound around the boundary portion with a proper tension, and the balloon tube and the string may be embedded in the tube of the catheter body.

BRIEF DESCRIPTION OF THE DRAWINGS

FIG. 1 is a sectional view of a balloon catheter according to an embodiment of the present invention;

FIG. 2 is a side view of the balloon catheter shown in FIG. 1;

FIG. 3 is a sectional view showing a balloon inflated state of the balloon catheter shown in FIG. 1;

FIG. 4 is a schematic view for showing a state wherein the balloon catheter is inserted in a blood vessel;

FIGS. 5A to 5C are perspective views for explaining the steps in manufacturing the balloon catheter shown in FIG. 1;

FIGS. 6A to 6E are sectional views for explaining the steps in mounting the balloon in the balloon catheter shown in FIG. 1;

FIGS. 7A to 7D are views for explaining the steps in embedding reinforcing members in the inner channels of the distal end portion of the catheter; and FIG. 8 is a sectional view of a balloon catheter according to another embodiment of the present invention.

BEST MODE FOR CARRYING OUT THE INVENTION

A preferred embodiment of the present invention will be described with reference to FIGS. 1 to 3.

FIG. 2 shows catheter body 1 made of a flexible tube. The flexible tube has flanged distal end portion $1a$ and annular groove $1b$ formed adjacent to distal end portion $1a$ along the circumferential direction of the tube. Catheter body 1 has first inner channel $1c$ open to the flange of distal end portion $1a$, as shown in FIG. 1, and second inner channel $1d$ open to the bottom of annular groove $1b$. First and second inner channels $1c$ and $1d$ extend along the longitudinal direction of catheter body $1b$.

Cylindrical balloon 2 is mounted in annular groove $1b$ of catheter body 1 so as to cover the bottom of groove $1b$. Balloon 2 is fixed by string 3 such that the balloon in the deflated state has an outer diameter equal to or smaller than maximum output diameter 1 of distal end portion $1a$ of catheter body 1. Therefore, the depth of groove $1b$ is large enough in consideration of the thickness of balloon 2.

Upper edge $1e$ of the wall surface defining annular groove $1b$ and contacting distal end portion $1a$ of catheter body 1 is formed as smooth curved surface.

A typical material of the catheter body is a thermoplastic resin such as polyolefin, an ethylenevinyl acetate copolymer, polyester, polyvinyl chloride, polyurethan, a fluorine resin, nylon, or the like.

A typical material of balloon 2 is an elastic material selected from silicone rubber, polyurethane, and latex.

An application method of this balloon catheter will be described below. As shown in FIG. 4, blood vessel inserter 4 (e.g., an indwelling cannula or an introducer) is partially pierced in blood vessel 5. Balloon catheter 6 is inserted into blood vessel inserter 4 and is gradually introduced into blood vessel 5.

During the above operation, since balloon 2 has a size equal to or smaller than the outer diameter of distal end portion $1a$ of catheter body 1, balloon 2 tends not to be caught by a check valve (not shown) arranged at insertion port $4a$ of inserter 4. Since the inner diameter of inserter 4 need not be larger than the outer diameter of the catheter, damage to the blood vessel can be reduced. Since distal end portion $1a$ of catheter body 1 has a substantially flat surface (or disk-like surface), the blood vessel wall is not stimulated and the catheter can be inserted to a desired indwelling position in blood vessel 5.

Carbon dioxide gas or another fluid is supplied to balloon 2 through second inner channel $1d$, and balloon 2 can be inflated to a predetermined size. The catheter can be inserted to the predetermined indwelling position, as shown in FIG. 3. Edge $1e$ of catheter body 1 has a smooth curved surface, and balloon 2 can be smoothly inflated without being interfered by edge $1e$, thereby obtaining a perfectly symmetrical shape of the inflated balloon. In order to deflate balloon 2 again, the fluid is removed from balloon 2 through second inner channel $1d$.

A method of manufacturing the balloon catheter will be described with reference to FIGS. 5A to 5C.

MANUFACTURING EXAMPLE

Polyvinyl chloride catheter body material 1' having four or five inner cavities each having a French size of 4 Fr to 8 Fr was prepared. Metal rods or metal pipes 9 and 10 were respectively inserted in pressure measurement cavity 7 and balloon inflation cavity 8 so as to leave them as inner channels, as shown in FIG. 5A. Polyvinyl chloride rods or pipes 11 and 12 made of the same material as that of catheter body 1 might be inserted in the other inner cavities, respectively. In this state, the diameter of the distal end portion of catheter body 1 was reduced to a predetermined value for a predetermined length (i.e., a length including the prospective balloon mounting portion and the prospective distal end formation portion extending toward the extreme end from it) by means of heat molding using a glass, ceramic or metal mold (FIG. 5B). This molding can also be made by ultrasonic or RF machining with a metal mold.

Stainless steel tubular member 13 which could be divided in its longitudinal direction was mounted on small-diameter portion 14 so as to cover the prospective balloon mounting portion, as shown in FIG. 5C. Prospective distal end formation portion 15 exposed from the upper end of tubular member 13 was molded with heat, an ultrasonic wave, or an RF wave by using a glass, ceramic or metal mold having a shape corresponding to distal end portion 1a of the catheter shown in FIG. 2, thereby obtaining a structure almost the same as that in FIG. 2. Tubular member 13 was divided and removed, and metal rods or metal pipes 9 and 10 were removed from the distal end of catheter body 1. Therefore, the pressure measurement cavity (corresponding to first inner channel 1c in FIG. 1) and the balloon inflation cavity (corresponding to inner channel 1d in FIG. 1) were formed.

Edge 1e contacting the balloon mounting portion (corresponding to annular groove 1b in FIG. 1) of distal end portion 1a of the catheter was molded with heat, an ultrasonic wave, or an RF wave together with a surface treatment using a solvent such as a tetrahydrofuran solution. As a result, a smooth curved surface was obtained (FIG. 2).

Metal, ceramic or heat-resistant plastic pipes or rods 17 and 18 having the same diameters as those of pressure measurement cavity 8 and balloon inflation cavity 7 are respectively inserted in cavities 7 and 8 so as to prevent their deformation (FIG. 6A). Latex balloon tube 2 having two open ends was inserted such that its one end covers distal end portion 1a, as shown in FIG. 6B. One end of balloon tube 2 was fixed by winding string 3 in annular groove 1b, as shown in FIG. 6C. An adhesive may be used in place of string 3 to fix the balloon tube, or string 3 may be wound around the balloon tube and may be fixed with an adhesive. A typical material of string 3 is a plastic material such as nylon. As an adhesive, a cyanoacrylate adhesive may be used.

As shown in FIG. 6D, balloon tube 2 was turned inside out and was moved in catheter body 1 so as to fit the other end of tube 2 on catheter body 1. As shown in FIG. 6E, the other end of balloon tube 2 was fixed in annular groove 1b and fixed through string 3 or an adhesive. Potting agent 16 was applied to a step formed between the fixing portion and catheter body 1. In this case, an urethane, epoxy, or silicone agent is preferably used as potting agent 16. Finally, pipes or rods 17 and 18 were removed. A balloon catheter shown in FIG. 1 was obtained without deforming pressure measurement cavity 11 and balloon inflation cavity 8. Balloon tube 2 was fixed to the catheter body such that tube 2 in the deflated state had a size equal to or smaller than maximum outer diameter of distal end portion 1a of catheter body 1. Therefore, the depth of groove 1b was large enough to receive balloon tube 2.

In the above example, potting agent 16 was filled in a stepped portion between the other end of balloon tube 2 and catheter body 1, and the other end was flattened. However, a proper tension may be applied to string 3, the other end portion of balloon tube 2 and string 3 may be embedded in catheter body 1, and the mounting portion may be flattened. In this case, potting agent 16 need not be used. If 20° nylon 6 string 3 is used, a proper tension is 5 to 50 g.

The outer diameter of mounted balloon 2 was equal to or smaller than the maximum outer diameter of the distal end portion of the catheter. When the balloon was inflated through the balloon inflation cavity, the shape was symmetrical.

In the above example, the diameter of the distal end portion of the balloon catheter was reduced by inserting pipes or rods having the substantially same diameters as those of the inner channels so as to prevent deformation of the first and second inner channels. After the operation, the pipes or rods were removed. However, in order to prevent natural contraction of the inner channels or deformation/contraction of the inner channels, which is caused by a pressure of the balloon mounting system, the following method may be employed.

As shown in FIG. 7A, first and second reinforcing members 19 and 20 are inserted beforehand in inner cavities 7 and 8 of balloon catheter body material 1' having a plurality of inner cavities. In this case, the portions 7a of inner cavities 7 and 8 which receive first and reinforcing members 19 and 20 have a larger thickness than that of other cavity portions by the thickness of reinforcing member 19 or 20, as shown in FIG. 7B. Reinforcing member 19 is located below distal end formation portion 1b' (FIG. 7C). The diameter of a distal end portion is reduced for a predetermined length by heat molding with a glass, ceramic or metal mold (FIG. 7C). In this case, molding may be performed with an ultrasonic or RF wave. Distal end 1a is molded with a glass or metal mold to obtain a mushroom-like shape while a stainless steel tubular member (FIG. 5C) dividable into two pieces in the longitudinal direction is inserted in the distal end portion. At this time, the uppermost end portion of reinforcing member 19 is preferably aligned with the distal end of the catheter. Heat molding, ultrasonic machining, or RF machining may be used. Balloon cavity 1d is located in a predetermined position.

One end of balloon 2 made of silicone rubber, urethane rubber or latex rubber is fixed to the distal end potion with a string, as shown in FIG. 1. The other end of balloon 2 is also fixed with a string, thereby completing molding and assembly of the distal end portion of the catheter shown in FIG. 1. According to the above method of the present invention, since the reinforcing members are inserted in the necessary inner cavity portions of the catheter, the inner cavities will not contract or will not be deformed during molding of the distal end of the balloon catheter and after molding. Therefore, degradation of balloon inflation/deflation response or measuring pressure response no longer occurs.

CAPABILITY OF EXPLOITATION IN INDUSTRY

A balloon catheter proposed by the present invention is useful for indwelling the distal end thereof in a predetermined portion of a blood vessel to perform any measurement and therapy.

We claim:

1. A balloon catheter comprising: a catheter body formed as a single member and made of a flexible tube provided with at least one inner channel with an opening at a distal end portion thereof, the catheter body being provided with an annular groove formed on an outer surface of the tube and including a distal wall adjacent to the distal end portion, a proximal wall, and a bottom portion extending a predetermined length along an axial direction of the tube between said distal and proximal walls, and with a balloon inflation inner channel open to said bottom portion of the annular groove; and a balloon secured to the catheter body for covering the bottom portion of the annular groove, the balloon being arranged in the annular groove such that an outer surface of a distal end portion of the balloon is contacted with, and is secured by a binding means to, the bottom portion of the annular groove adjacent said distal wall, with the rest of the balloon being everted over said binding means, with the proximal end of the balloon secured near the proximal wall, with the entire outer diameter of the balloon in its deflated state being equal to or smaller than a maximum outer diameter of the distal end portion of the tube.

2. A catheter according to claim 1, wherein an outer edge of said distal wall is a smooth curved surface.

3. A catheter according to claim 1, wherein the distal end portion has a smooth curved surface or is flat.

4. A catheter according to claim 1, wherein a cylindrical reinforcing member having an inner passage is coaxially inserted in a portion of the at least one inner channel over which the balloon is mounted, said inner passage being in communication with other portions of the at least one inner channel.

5. A catheter according to claim 4, wherein said reinforcing member has substantially the same inner diameter as that of the at least one inner channel and is connected thereto through a substantially smooth surface.

6. A catheter according to claim 4, wherein the reinforcing member is made of a heat-resistant hard plastic material.

7. A catheter according to claim 4, wherein the reinforcing member is made of a metal.

8. A catheter according to claim 4, wherein the reinforcing member is made of ceramics.

9. A balloon catheter according to claim 1, wherein the outer diameter of the balloon in its deflated state is equal to a maximum outer diameter of the distal end portion of the tube.

10. A balloon catheter according to claim 1, wherein said binding means is a winding of a string.

11. A balloon catheter according to claim 1, wherein said binding means is an adhesive.

12. A balloon catheter according to claim 4, wherein said cylindrical reinforcing member has a length extending from the distal end portion of the balloon to a proximal end portion of the balloon secured to the annular groove.

* * * * *

UNITED STATES PATENT AND TRADEMARK OFFICE
CERTIFICATE OF CORRECTION

PATENT NO.   : 5,042,976
DATED        : August 27, 1991
INVENTOR(S)  : ISHITSU et al It is certified that error appears in the above-identified patent and that said Letters Patent is hereby corrected as shown below:

TITLE PAGE -

Section [56] References Cited, left column, change

U.S. Patent "3,143,651" to --4,143,651--.

Signed and Sealed this

Twenty-second Day of June, 1993

Attest:

MICHAEL K. KIRK

*Attesting Officer*    *Acting Commissioner of Patents and Trademarks*